US006878555B2

(12) United States Patent
Andersson et al.

(10) Patent No.: US 6,878,555 B2
(45) Date of Patent: Apr. 12, 2005

(54) METHOD AND INSTRUMENTATION FOR MICRO DISPENSATION OF DROPLETS

(75) Inventors: Per Andersson, Uppsala (SE); Gérald Jesson, Stockholm (SE); Tobias Söderman, Uppsala (SE); Jan Sjöberg, Uppsala (SE)

(73) Assignee: Gyros AB, Uppsala (SE)

( * ) Notice: Subject to any disclaimer, the term of this patent is extended or adjusted under 35 U.S.C. 154(b) by 505 days.

(21) Appl. No.: 10/004,424

(22) Filed: Dec. 6, 2001

(65) Prior Publication Data

US 2003/0094502 A1 May 22, 2003

(30) Foreign Application Priority Data

Oct. 21, 2001  (SE) .............................................. 0103522
Dec. 5, 2001   (SE) .............................................. 0104077

(51) Int. Cl.[7] .................................................. G01N 1/10
(52) U.S. Cl. ........................... 436/180; 436/45; 436/50; 436/54; 436/161; 436/179; 422/64; 422/67; 422/70; 422/72; 422/100; 422/102
(58) Field of Search .............................. 436/45, 50, 54, 436/161, 179, 180; 422/64, 67, 70, 72, 100, 102

(56) References Cited

U.S. PATENT DOCUMENTS

| | | | |
|---|---|---|---|
| 6,063,589 A | | 5/2000 | Kellogg et al. |
| 6,121,048 A | * | 9/2000 | Zaffaroni et al. .............. 436/45 |
| 6,143,247 A | * | 11/2000 | Sheppard et al. .............. 422/63 |
| 6,192,768 B1 | | 2/2001 | Wallman et al. |
| 6,338,820 B1 | * | 1/2002 | Hubbard et al. .............. 422/64 |
| 6,342,395 B1 | | 1/2002 | Hammock et al. |
| 6,395,562 B1 | | 5/2002 | Hammock et al. |

FOREIGN PATENT DOCUMENTS

| | | |
|---|---|---|
| EP | 0 601 714 A1 | 6/1994 |
| WO | WO 00/79285 A2 | 12/2000 |
| WO | WO01/30500 A1 | 5/2001 |

OTHER PUBLICATIONS

Laurell et al., J. Micromech. Microeng., vol. 9 (1999) pp. 369–376.

(Continued)

*Primary Examiner*—Jan M. Ludlow
(74) *Attorney, Agent, or Firm*—Birch, Stewart, Kolasch & Birch, LLP.

(57) ABSTRACT

A method for dispensing droplets of a liquid to a microsystem in the form of a disc comprising a target area (TA°I) in its surface, said disc preferably being a microfluidic disc comprising a microchannel structure with an inlet port that is a target area (TA°I). The method is characterized by comprising the steps of:
i) providing (1) said disc which has a triggering mark, and (2) a dispenser arrangement comprising:
  a) a spinner for rotating the disc around its axis,
  b) a drop dispenser permitting dispensation of droplets to inlet port I,
  c) a fixed trigger position outside the disc, and
  d) a controller which is capable of triggering the dispensation of a droplet into (TA°I) as a function of the triggering mark passing the trigger position,
ii) placing the disc in the spinner and programming the controller with values for dispensing parameters that will give dispensation of the droplets to TA°I,
iii) dispensing the droplets.

Figure 1A:
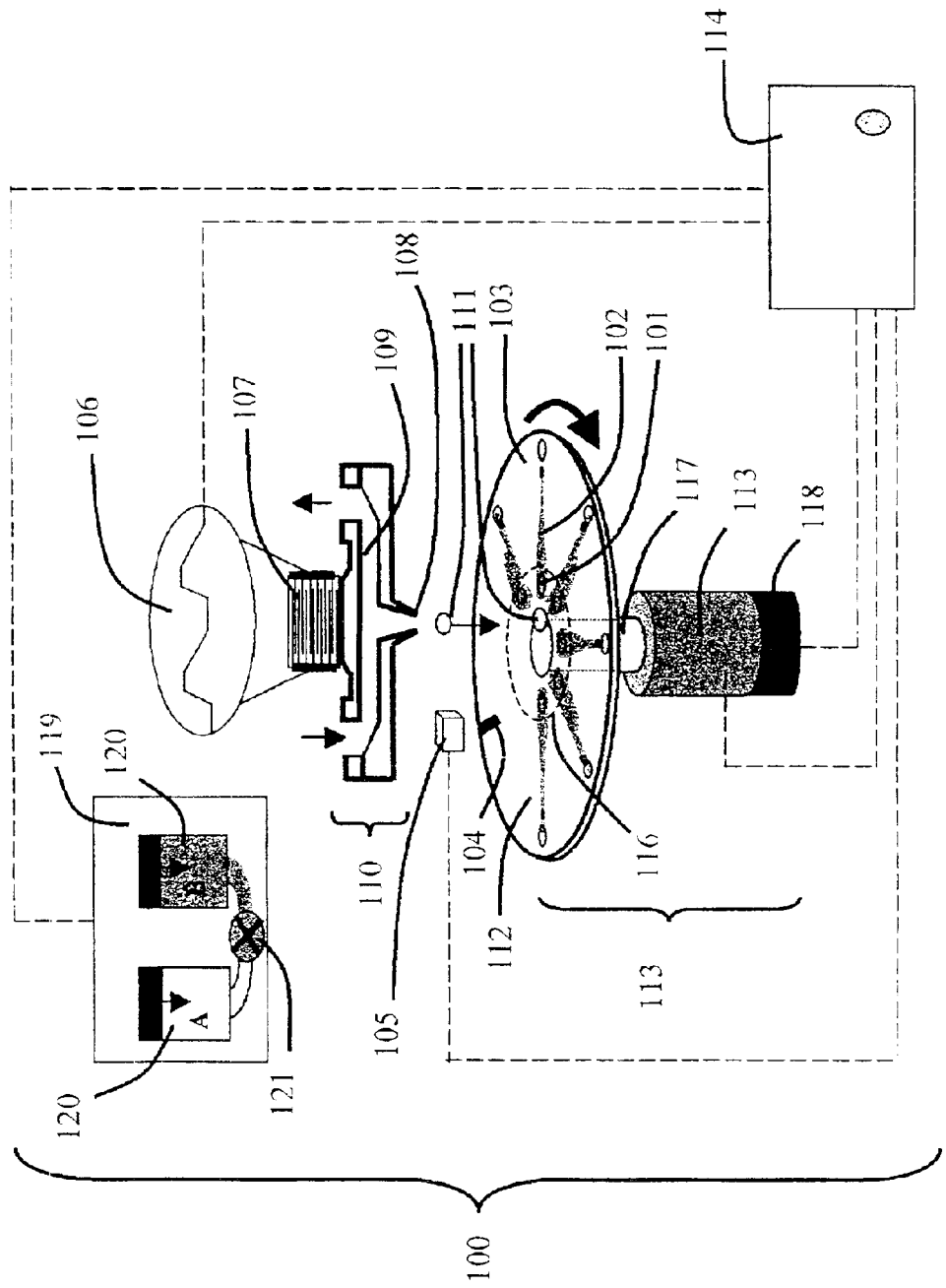

The invention also comprises the dispenser arrangement as such.

25 Claims, 6 Drawing Sheets

OTHER PUBLICATIONS

Nilsson et al., Anal. Chem., vol. 67 (1995) pp. 3051–3056.

Sziele et al., J. Chromatography, vol. 669 (1994) pp. 254–258.

Lemmo et al., Anal. Chem., vol. 69 (1997) pp. 543–551.

Schober et al., BioTechniques, vol. 15, No. 2 (1993) pp. 324–329.

Ekstrand et al., Micro Total Analysis Systems 2000, A. van den Berg et al. (eds) (2000) pp. 311–314.

Horacio Kido et al., Analytica Chimica Acta, vol. 411 (2000) pp. 1–11.

* cited by examiner ing CD" in Proceedings of µ-TAS 2000 Symposium 14–18 May, 2000, Enschede, the Netherlands, Eds van den Berg et al., Kluwer Academic Publisher).

METHOD AND INSTRUMENTATION FOR MICRO DISPENSATION OF DROPLETS

TECHNICAL FIELD

The present invention concerns an interface between the macro and the micro world with respect to the dispensation of droplets of a liquid to one or more target areas ($TA^0I$, $TA^1I$, $TA^2I$ etc, array of target areas) on the surface of a disc. The target areas together with the disc define a microsystem for handling liquid aliquots in the microformat. The disc is preferably a microfluidic disc.

Microformat in this context means that the liquid aliquots are in the microliter ($\mu$l) range. This range includes the nanoliter (nl) range which includes the picoliter (pl) range.

BACKGROUND TECHNOLOGY AND PUBLICATIONS

An increasing number of microsystems have been presented during the last decade. The main focus of microscaling has been the analytical and/or preparative performance of these microsystems and in practice very little attention has been paid on interfacing these microworlds with the surrounding macroworld. The present invention presents an interfacing solution and concerns dispensation of liquid to microsystems comprising one, two or more target areas.

Previous microfluidic systems have typically comprised one, two or more microchannel structures in which liquids are transported and processed. Variants that can be spun around an axis of symmetry for driving liquid flow within the structures have been suggested previously, e.g. circular forms and other kinds discs having an axis of symmetry.

Modifications of traditional ink-jet technology have been suggested to accomplish liquid dispensation to target areas in microsystems. In most cases the dispensing unit has been linked to a liquid reservoir (Sziele at al., "*Adaption of a microdrop injector to sampling in capillary electrophoresis*", J. Chromatogr. A 669 (1994) 254–257; Schober et al., "*Accurate high-speed liquid handling of very small biological samples*", Biotechniques 15 (1993) 2; Nilsson et al., "*Thin-layer immunoaffinity chromatography with bar code quantitation of C-reactive protein*", Anal. Chem. 67 (1995) 3051–3056; Wallace et al., "*Ink-jet based fluid microdispensing in biochemical applications*", Lab. Automation News 1(5) (1996) 6–9; and Lemmo et al., "*Characterization of an inkjet chemical microdispenser for combinatorial library synthesis*" Anal. Chem. 69 (1997) 543–551). Some years ago a versatile through-flow channel microdispenser that could be adapted for dispensation to microsystems was presented (Laurell et al., "*Flow-through sampling cell and use thereof*" U.S. Pat. No. 6,192,768, Gyros AB) and later further developed (Laurell et al., "*Design and development of a silicon microfabricated flow-through dispenser for on-line picoliter sample handling*", J. Micromech. Microeng. 9 (1999) 369–376; Thornell et al., "*Desk top microfabrication— Initial experiments with a piezoceramic*", 9 (199) 434–437; Tormod et al., "*Device for dispensing droplets*", WO 0130500, Gyros AB and Stjernström et al., "*A multi-nozzle piezoelectric microdispenser for improving the dynamic volumetric range of droplets*" in Proceedings of µ-TAS 2000 Symposium 14–18 May, 2000, Enschede, the Netherlands, Eds. van den Berg et al., Kluwer Academic Publisher).

The flow-through sampling cell developed by Laurell et al (supra) has been suggested for dispensing droplets to microfludic discs (Ekstrand et al., "*Microfluidics in a rotat-*

Previously liquid aliquots in the microliter ($\mu$l) range have been dispensed to individual target areas of resting discs. Spinning (centrifugal force) has been used to control the motion of the liquid into and within the structures. This dispensation procedure is tedious and suffers from a number of drawbacks, in particular if dozens of microstructures have to be fed before spinning. Many of the drawbacks become more accentuated when going down to dispensation of nl- and pl-volumes.

Dispensation while spinning a microsystem has the potential of feeding large numbers of target areas at the same time solving the problem of interconnecting hundreds of target areas. Interconnecting is tedious and has not yet been achieved in standard microfabrication procedures (Ellis Meng et al., "*Micromachined fluidic couplers*" and Aniruddha Puntambekar et al., "*Self-aligning microfluidic interconnects with low dead volume*" in Proceedings of µ-TAS 2000 Symposium 14–18 May, 2000, Enschede, the Netherlands, Eds van den Berg et al., Kluwer Academic Publisher).

Dispensation of liquid aliquots during spinning is associated with targeting problems that are not at hand when the disc is resting because during spinning the target area is moving.

Dispensation of droplets to a spinning microfluidic disc has been presented in a poster after the priority date of the present invention. See Jesson & Andersson "Multiple separations at nanoliter scale using gradient elution" in Proceedings of µ-TAS 2001 Symposium, Oct. 21–25, 2001, Monterey, USA, Eds. Ramsey and Van der Berg (20001) Kluwer Academic Publisher. The poster can be downloaded from w.w.w.gyros.com.

OBJECTS OF THE INVENTION

A first object is to provide an instrument set up (arrangement) and a method which enable dispensation of liquid droplets to inlet ports of individual target areas of a disc-shaped microsystem without:
(a) the need of physically interconnecting the target areas with the dispensing device and
(b) the variability caused by differential evaporation from target areas that are loaded with liquid while the disc is resting.

A second object is to provide an instrument set up (arrangement) and a method which enable dispensation of droplets to the target areas of a disc-shaped microsystem while spinning the microsystem, which is preferably in the form of a microfluidic disc. Suitable spin speeds are >0 rpm, for instance $\geq 25$ rpm, such as $\geq 50$ rpm or $\geq 100$ rpm or $\geq 1000$ rpm, and are typically $\leq 15\ 000$ rpm or $\leq 20\ 000$ rpm. The droplet size should be uniform for one and the same liquid with a suitable size within the range of $10^{-6}$–$10^0$ µl, such as $10^{-5}$–$10^{-1}$ µl and/or $\leq 10^{-1}$ µl or $\leq 10^{-2}$ µl or $10^{-3}$ µl or $10^{-4}$ µl.

A third object is to provide an instrument set up (arrangement) and a method, which enable interacing a liquid separation/analytical device (such as a chromatography system, electrophoresis system, etc.) or a liquid system evoluting with the time (such as a fermentor) with a spinning microsystem in the form of a disc.

A fourth object is to provide an instrument set up (arrangement) and a method, which enable transferring of a gradient of a liquid formed in the macroworld into the individual target areas of a microsystem in the form of a disc, preferably a microfluidic disc. This object also includes applying the transferred gradient to an experiment that is performed within the microsystem. The term "gradient of a liquid" means that there is a change in composition of the liquid as a function of time. The experiments may be of the same kind as discussed under the heading "Microfluidic Discs and Processes to be Performed" below.

FIGURES

Figure 1B:
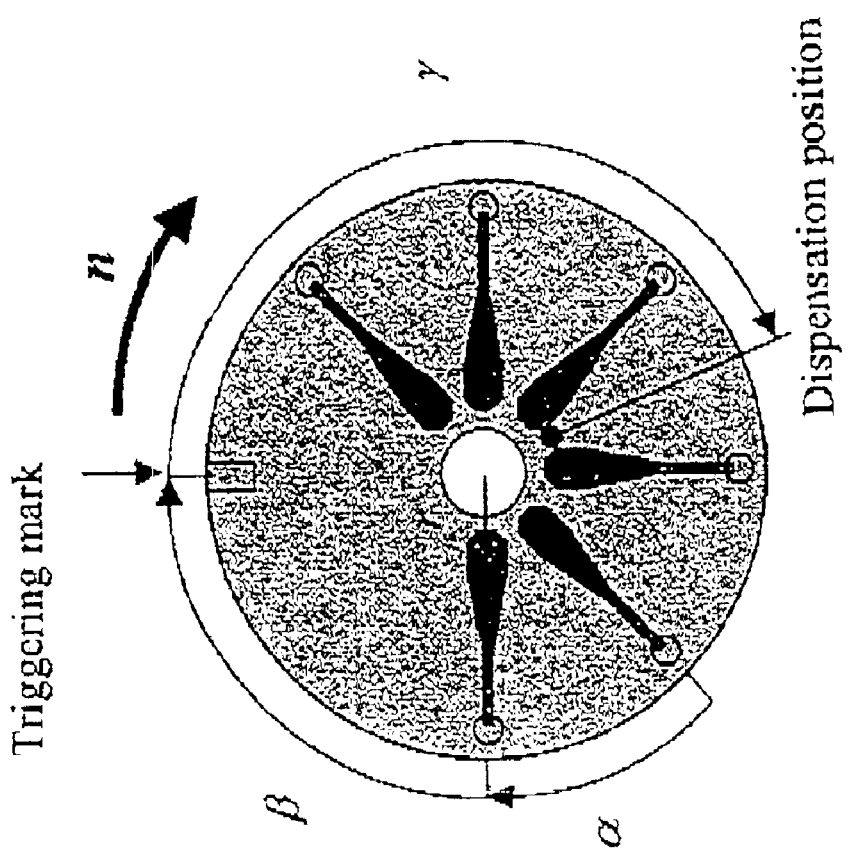

FIGS. 1a and b illustrate a variant of the instrumentation set up (arrangement) of the present invention. In FIG. 1b dispensation position corresponds to the position of the orifice.

Figure 2:
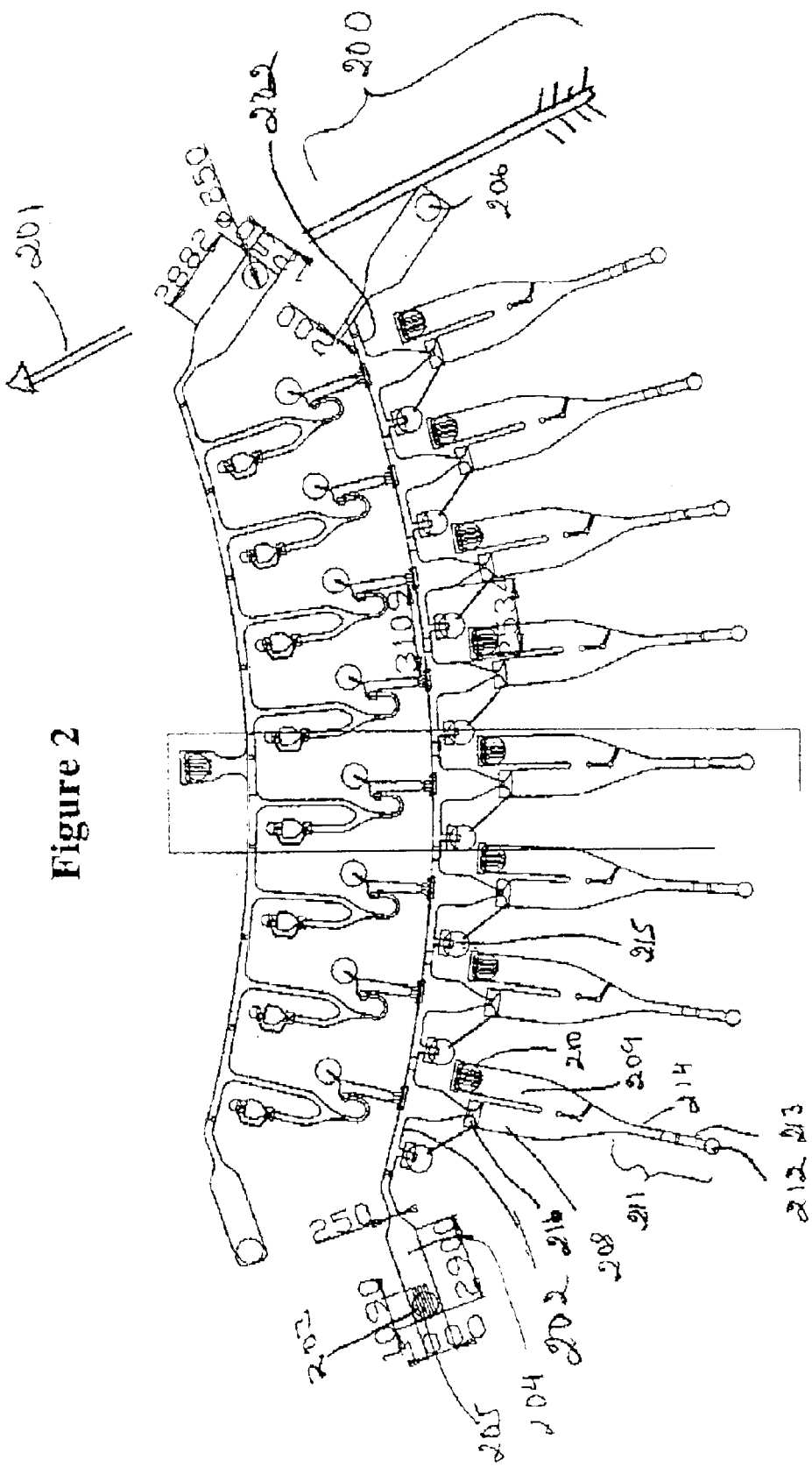

FIG. 2 gives the microfluidic structures of the disc used in experiment 5.

Figure 3:
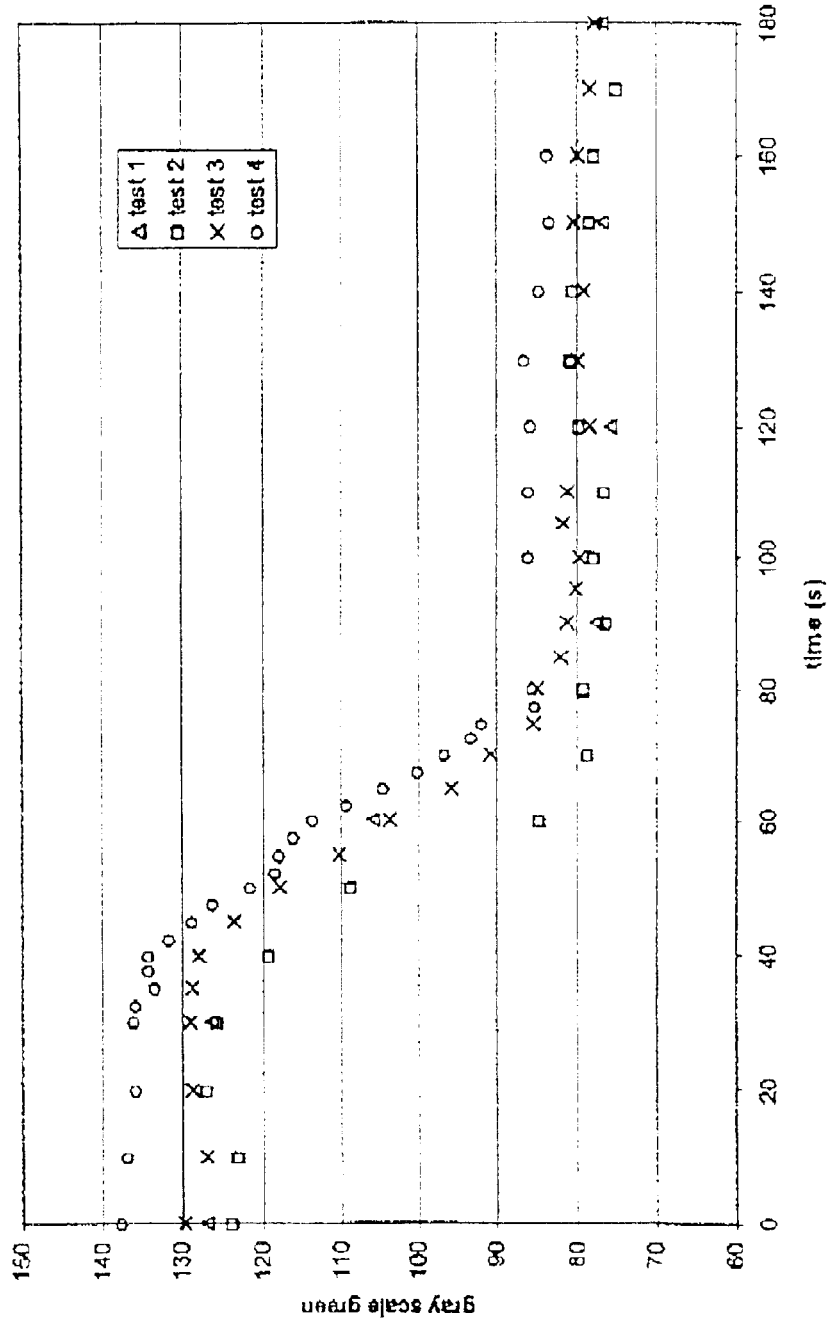

FIG. 3 refers to results obtained for experiment 1.

Figure 4:
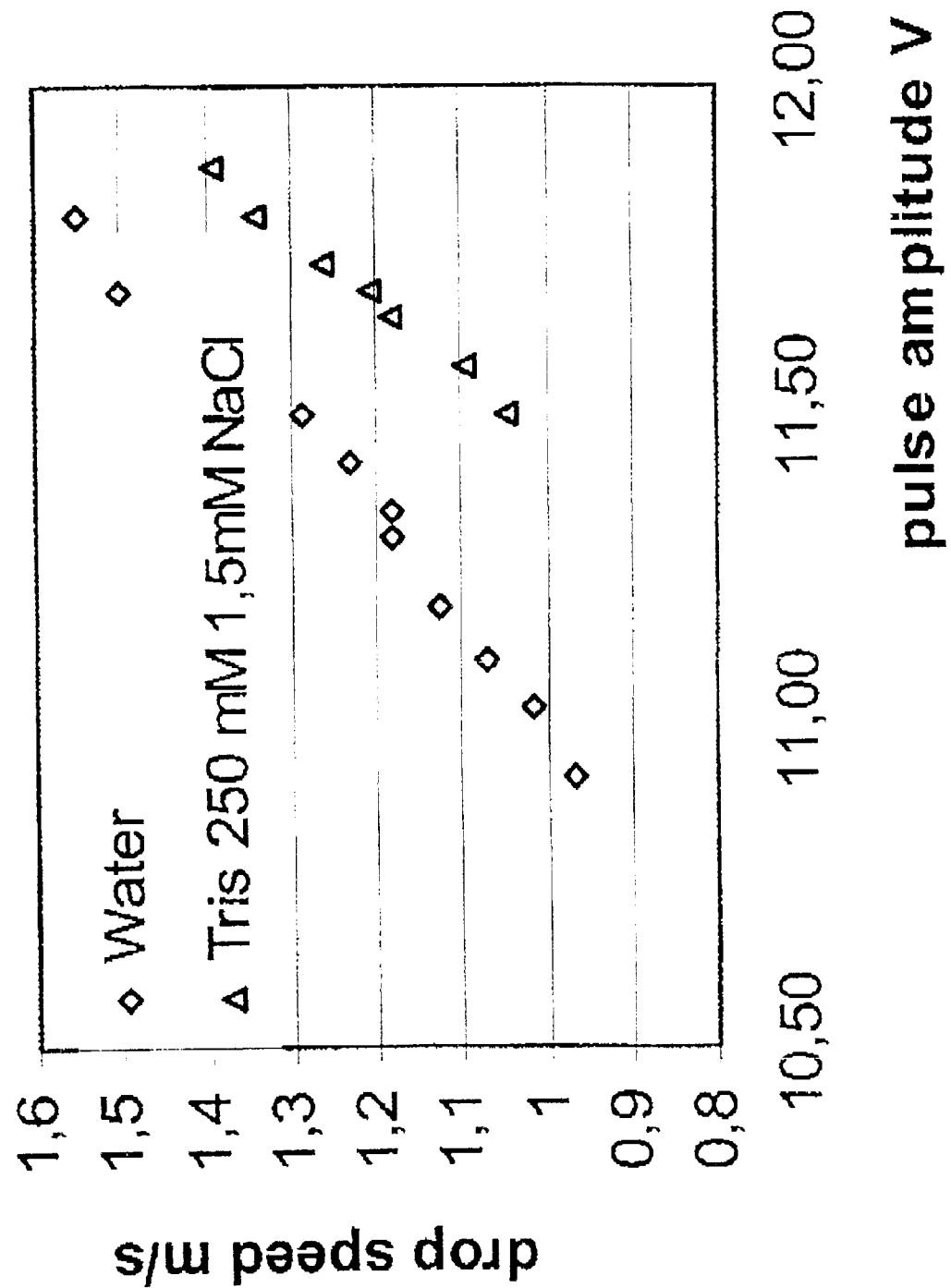

FIG. 4 refers to results obtained for experiment 2.

Figure 5:
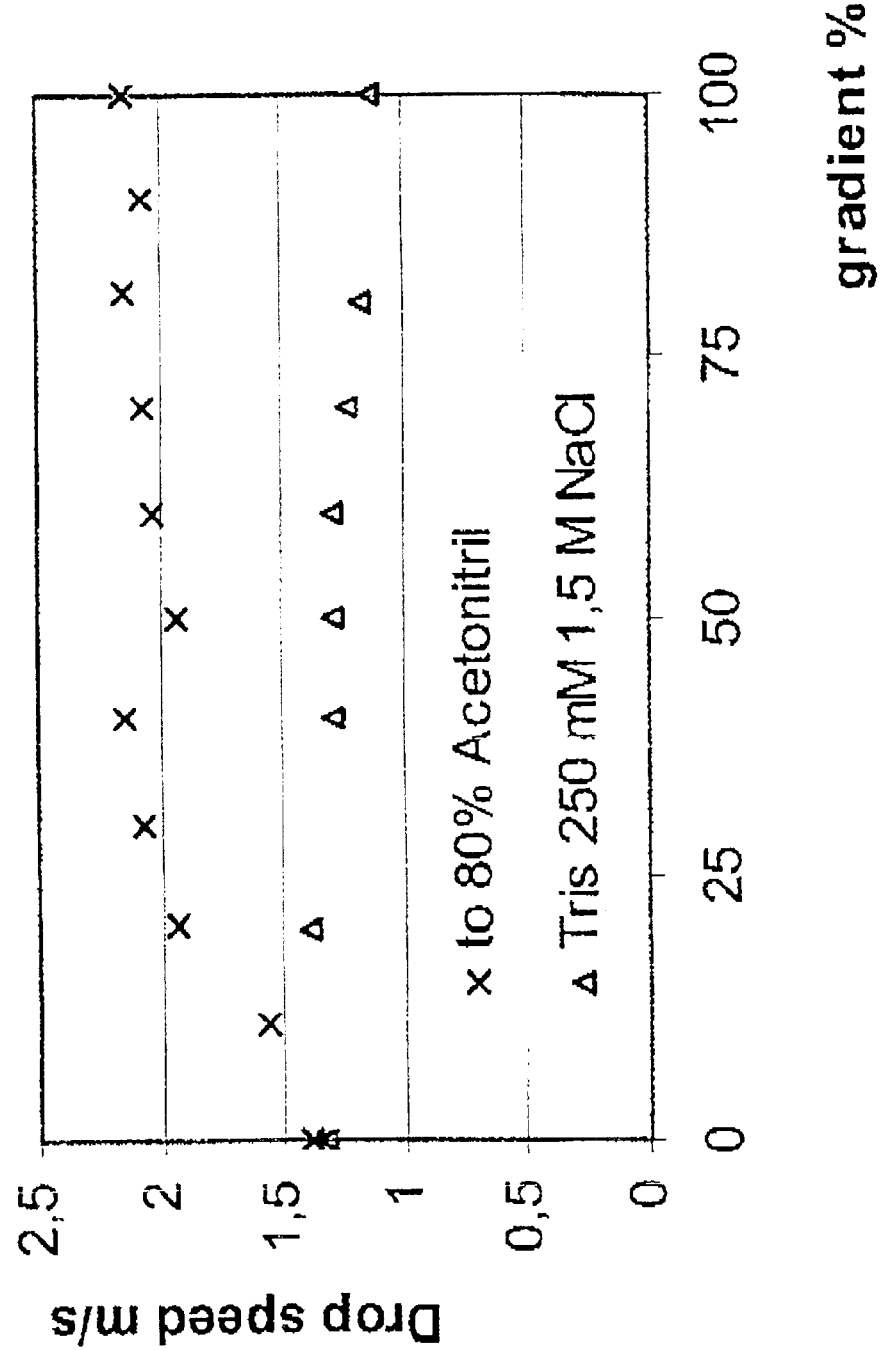

FIG. 5 refers to results obtained for experiment 3.

THE INVENTION

The inventors have carefully evaluated the parameters that may influence the trajectory path of a sequence of droplets that are ejected through an orifice towards a spinning surface containing separate target areas for the individual droplets. The system configuration (100) is given in FIG. 1a which illustrates the inventive concept in relation to a microfluidic disc.

The inlet ports (101) (TA$^0$I, TA$^1$I, TA$^{21}$ etc) of x individual microchannel structures (102) are separated on the microfluidic disc (103) by an angle α radians. The inlets are at a radial distance r from the centre of the disc, rotating at n rpm (FIG. 1b). The angular velocity ω of the disc is determined by the equation:

$$\omega = 2\pi n/60 \text{ in rad/s} \quad \text{(eq 1)}$$

When a triggering mark (104) on the disc passes a detector at a fixed trigger position (105), a dispensing signal (106) comprising a predetermined number of dispensing pulses with a frequency of f Hertz is sent to a dispensing actuator (107). The number of pulses is equal to the number of structures x into which droplets are to be dispensed for the subsequent revolution (one droplet per target area). The actuator (107) is associated with the wall of the flow-through channel (109) and is in FIG. 1a placed opposite the orifice (108) of the dispenser (110) so that droplets (111) can be ejected perpendicular towards the surface (112) of the disc (103) at the frequency of f Hertz. The fixed trigger position (105) and the first structure into which the first droplet must enter are separated by an angle of β radians. The orifice (108) of the dispenser (110) is positioned above the surface (112) and at a distance of γ radians from the trigger position (105). The radial position of the orifice relative to the disc is typically the same as for the inlet ports (TA$^0$I, TA$^1$I, TA$^{21}$ etc) (101). It is possible to determine the time $T_{trig}$ between the time at which the triggering mark passes the fixed trigger position and the time at which a predetermined inlet port passes in front of the orifice (after a predetermined number of complete rotations p) by the following equation:

$$T_{trig} = [(\beta+\gamma)/\omega] + [2\pi \cdot p/\omega] \text{ in s} \quad \text{(eq 2)}$$

The dispenser is located at a fixed point, h meters above the disc (typically less than a half centimeter). The droplets are shot at a speed v, which is dependent on the pulse shape including amplitude and frequency f and the characteristics of the liquid. The system typically has a delay $T_{elec}$ between the time at which the triggering mark passes in front of the trigger position and the actual ejection of the first droplet caused by a dispensing signal (in a revolution). $T_{elec}$ always contains one part that is inherent in the system and therefore constant and one optional part that is controlled by the operator and thus changeable. The droplet velocity $v_{hit}$ necessary to permit the ejected droplet to enter the microstructure can be determined by the equation:

$$v_{hit} = h/[T_{trig} - T_{elec}] \text{ in m/s} \quad \text{(eq 3a)}$$

$$v_{hit} = h/[((\beta+\gamma)/\omega) + (2\pi \cdot p/\omega) - T_{elec}] \text{ in m/s} \quad \text{(eq 3b)}$$

If we consider that v is constant throughout the droplet trajectory, the dispensing frequency f required for each droplet to reach the successive inlet port (TA$^0$I, TA$^1$I, TA$^2$I etc) is determined by:

$$f = \omega/\alpha \text{ in hertz} \quad \text{(eq 4)}$$

In the case the composition of the liquid changes during the dispensation, physico-chemical characteristics of the liquid may also change. This may influence the velocity with which a droplet leaves the dispenser orifice and as described in equation 3 will change the actual target for the droplet if no other parameters are changed. See experiment 2 of the experimental part. In such a case it will be necessary to secure the dispensation by adjusting parameters as is described for the present invention.

The Method Aspect of the Invention (First Aspect).

The first aspect of the invention is a method for dispensing droplets of a liquid to a microsystem in the form of a disc comprising a target area (TA$^0$I) in its surface. The disc is preferably a microfluidic disc comprising a microchannel structure with an inlet port that is the target area (TA$^0$I) o the structure. The method is characterized in comprising steps (i)–(iii) where Step (i) is to provide (1) a disc as defined elsewhere in this specification which has a triggering mark from which the angular position of any other part of the disc is defined, and (2) the innovative dispenser arrangement described herein.

Step (ii) is to place the disc in the arrangement and program a controller of the arrangement with values for dispensation parameters which will secure dispensation of a droplet into said target area (TA$^0$I). Programming can be done before or after the disc is placed in the arrangement.

Step (iii) is to permit the arrangement to proceed with the dispensation, for instance by pressing a start button.

The arrangement can be designed for dispensation in various directions, e.g. downward with the disc below the orifice of the disc, upward with the disc above the orifice, lateral with the disc oriented vertically etc. The dispensation direction is preferably perpendicular to the surface of the disc.

The characteristic features of the invention will now be described in reference to a microfluidic disc. The principles outlined will be applicable also to discs containing non-fluidic microsystems. An important exception is that the processes to be carried out within non-fluidic microsystems should not be carried out under flow conditions since these systems have no microchannels in which liquid can be transported away from the target areas.

The liquid to be dispensed may be a homogeneous solution or a suspension, an emulsion or a dispersion. Dispersed/suspended particles may be biological, for instance cells and viruses or parts thereof that are in particle form, solid phases that are in particulate form as described under the heading "Microsystems (discs) provided in step (i)", etc. Solid phases in particulate form are typically dispensed in order to create a packed bed within a microchannel structure.

Microsystems (Discs) Provided In Step (I).

The term "microsystem" comprises systems in which the target areas for droplet dispensation are present in the surface of a disc. The term comprises microfluidic systems and systems in which the target areas are not part of any fluidic system. The term "target area" includes that a dispensed liquid shall be processed within the target area and/or in a microchannel structure associated with the target area. Thus for microfluidic system a target area (TA) means an inlet port of a microchannel structure. An array of target areas in the form of isolated wells in the micro-format is an example of a microsystem that is not fluidic (e.g. a microtiter plate).

The individual target areas typically have sizes $\leq 2.5 \times 10^1$ mm$^2$, such as $\leq 10^0$ mm$^2$ or $\leq 10^{-1}$ mm$^2$ or $\leq 10^{-2}$ mm$^2$ or $\leq 10^{-3}$ mm$^2$. The lower limit is typically $\geq 10^{-5}$ mm$^2$, such as $\geq 10^{-4}$ mm$^2$ or $\geq 10^{-3}$ mm$^2$ or $\geq 10^{-2}$ mm$^2$. The exact possible interval is determined by the accuracy in the dispensing parameters.

The terms "microfluidic disc", "microfluidic system", "fluidic microsystem" etc mean a disc, which comprises at least one microchannel structure through which one or more liquid aliquots (droplets) are transported and/or processed in various kinds of microcavities (reaction microcavities). The result of the processing is measured in one or more detection microcavities through corresponding detection areas, which are placed in either or both of the surfaces of the disc. Reaction microcavities and detection microcavities may coincide. The interior of a microchannel structure is in contact with ambient atmosphere through inlet and/or outlet openings and/or vents. Other parts of the structures are normally separated from direct contact with ambient atmosphere by the material of the disc. The inlet ports of the microchannel structures of a microfluidic disc/system define an array of target areas.

Microformat means that the liquid aliquots that are transported within the device has a volume in the $\mu$l-range, i.e. $\leq 1000$ $\mu$l such as $\leq 100$ $\mu$l or $\leq 50$ $\mu$l and includes the nl-range (nanoformat), such as $\leq 500$ nl or $\leq 100$ nl or $\leq 50$ nl or $\leq 10$ nl.

The disc concept includes circular discs, discs with an n-numbered axis of symmetry ($C_n$) where n is an integer 3, 4, 5, 6 or larger and bodies with one planar surface and a non-planar surface on the opposing side of the disc.

The disc used in the invention comprises a triggering mark (104), which is at a distinct position on a rotating part of the disc, preferably associated with the circumference of the disc, for instance the edge or an annular zone close to the edge.

A microfluidic disc typically comprises one, two or more microchannel structures, such as $\geq 10$, or $\geq 50$ or $\geq 100$ microchannel structures. For discs in which there is a plurality of the structures, the structures may be identical or different, for instance with at least one of the structures being different from the other. An inlet port (TA I) that is to be used for dispensation according to the invention typically is located at the same radial distance for more than one microchannel structures. The microchannel structures in a disc may be arranged in subgroups such that all TA is in a subgroup are at the same radial distance but for different subgroups at different radial distances. The target areas may also be arranged in a spiral-like manner around the axis of symmetry of the disc.

The term "microchannel structure" contemplates that the structure comprises one or more cavities/chambers and/or channels that have a cross-sectional dimension that is $\leq 10^3$ $\mu$m, preferably $\leq 10^2$ $\mu$m. The volumes of cavities/chambers are typically $\leq 1000$ nl, such as $\leq 500$ nl or $\leq 100$ nl or $\leq 50$ nl or $\leq 25$ nl. This in particular applies to the detection and/or reaction microcavities. Chambers/cavities directly connected to to inlet ports for liquids may be considerably larger, e.g. microchambers/microcavities intended for application of sample and/or washing liquids.

The transport of liquid within the microchannel structures may be driven by various forces, for instance inertia force such as centrifugal force, electrokinetic forces, capillary forces, hydrostatic forces etc. Pumps of various kinds may be used. Typically centrifugal force and/or capillary force are utilized at inlet ports.

The disc may be made from different materials, such as plastic material, glass, silicone etc. Polysilicone is included in plastic material. From the manufacturing point of view plastic material is many times preferred because this kind of material are normally cheap and mass production can easily be done, for instance by replication. Typical examples of replication techniques are embossing, moulding etc. See for instance WO 9116966 (Pharmacia Biotech AB, Öhman & Ekström). Replication processes typically result in open microchannel structures as an intermediate product which subsequently is covered by a lid, for instance according to the procedures presented in WO 0154810 (Gyros AB, Derand et al) or by methods described in publications cited therein. The proper hydrophilic/hydrophobic balance are preferably obtained according to the principles outlined in WO 0056808 (Gyros AB, Larsson et al) and WO 0147637 (Gyros AB, Derand et al). All three WO publications are hereby incorporated by reference.

The microchannel structures (200) used in experiments 4–5 of the Experimental Part is given in FIG. 2. The arrow (201) indicates the upward direction and is directed towards the centre of the disc on which the structure is placed. The complete structure used in the experiments comprises a common distribution channel (202) with an inlet port (203) and an inlet microcavity (204) with parallel grooves/ridges (205) in the bottom, and an outlet port (206). Along the distribution channel (202) there is a number of Y-shaped structures (microchannel structures) (200) with one of the upward shanks (208) being connected to the distribution channel (202) and the other upward shank (209) comprising an inlet port (210) of the same kind as inlet port (203). The lower shank (211) of the Y-shaped structure contains an outlet port (212) opening to ambient atmosphere and has a shallow part (213) and a deeper part (214). The dual depth means that if a liquid containing particles with a larger diameter than the depth of the shallow part is transported through the structure, the particles will assembly as a packed bed in the deeper part (214) immediately upstream the shallow part (213). The common distribution channel (202) comprises vents (215) to ambient atmosphere between the individual microchannel structures. The inner surfaces of these vents are hydrophobized in order to prevent leakage of liquid. There are valves (216) in form of hydrophobized inner surfaces between each microchannel structure and the common distribution channel.

In the experiments 4 and 5 in the Experimental Part, the part occupied by the packed bed (214) corresponds to a reaction microcavity and/or a detection microcavity. The part of the structure that is above the common distribution channel was not used in experiment 1 and 2 and is therefore not further described.

The Dispenser Arrangement (Instrumentation Set Up) Provided in Step (i).

The arrangement constitutes a second aspect of the invention.

The dispenser arrangement comprises:
a) a spinner (113) for rotating the disc (103) around its axis,
b) a drop dispenser (110) permitting dispensation of droplets (111) to inlet port I (TA I) (101) through a dispenser orifice (108),
c) a fixed trigger position (105) with a detector, and
d) a controller (114) which is capable of initiating dispensation of a droplet into inlet port I (111) as a function of the triggering mark (104) passing the trigger position (105).

Description of the Various Parts of the Arrangement
a) The spinner

The spinner (113) comprises a motor (115) and a disc holder (116) with a shaft (117) for rotating the disc around its axis. An encoder (118) may be linked to the shaft and grades a revolution into minor parts, for instance into $\geq 10\,000$ grades such as $\geq 20\,000$ grades or $\geq 30\,000$ grades. The encoder may alternatively be associated with the disc.

The spinner should in the preferred variants permit spinning that can be regulated within at least parts of the intervals given under the heading "Objects of the invention", and stepwise rotation of the shaft and the disc.

b) Drop Dispenser and Liquid Transport to and Through the Dispenser.

The drop dispenser (110) shall be capable of dispensing droplets to the inlet port I (TA I) (101) at controllable frequencies and of controllable volumes and velocities (m/s) through the dispenser orifice (108).

The drop dispenser comprises the channel (109) for transporting liquid to the orifice (108) from which droplets can be dispensed. In the typical case the drop dispensers used in ink-jet printers can be applied to the drop dispensers that are used in the present invention, if appropriately modified. Compare the discussion under the heading "Background Technology and Publications".

One kind of suitable drop dispensers has a head with a flow-through channel along which there is a dispensing orifice with which a dispensing actuator is associated, for instance with the channel wall essentially opposite to the orifice. See for instance the dispenser given in FIG. 1a. The actuator typically is sensitive to pressure pulses and/or electrical pulses meaning that each pulse of sufficient amplitude will eject a droplet through the orifice. In an advantageous variant, the actuator comprises a piezoelectric element enabling well-defined and short dispensing pulses for the dispensation of droplets. This kind of drop dispensers is previously known. See the publications cited above in the name of Laurell et al., Thornell et al, Tormod, Stjernström et al., and Ekstrand et al.

An alternative dispenser variant comprises a liquid transport channel ending in a dispenser orifice and has a dispensing actuator associated with the channel in an upstream position relative to the orifice. The actuator may be ring-formed and fully or partially embracing the liquid flow passing through the channel. In case electrical pulses are used for droplet formation the ring may comprise a piezoelectric material. This kind of drop dispensers is available from Cartesian (England) and can be used in the present invention if properly modified. Other candidate dispensers are based on the bubble-jet principle developed for example by Olivetti (Italy), or based on other pieozoelectric transducers or speakers available from MicroFab (USA) and/or based on continuous mode ink-jet working according to Rayleigh breakup principle and/or where droplets are directed under a deflection field.

Flow-through dispensers have the advantage that the composition of the liquid easily can be changed. This can be accomplished by allowing a discrete train of different liquids (stepwise gradient) or a continuous gradient to pass through the channel and programming the controller appropriately. When the sufficient amount of droplets of a certain composition has been dispensed, dispensing can be halted until a liquid of desired composition comes into dispensing position. By using flow-through dispensers the replacement of liquid will be facilitated. The dispenser variants described in the preceding paragraph typically require more complex design and/or complicated procedures for replacing the dispensing liquid or deflecting droplets under an electric field (necessitating the droplets to be charged).

The drop dispenser may be linked to a pump (119) for driving the liquid through the channel from one or more reservoirs (120) containing the same or different liquids. By including valves (121) at the junction of conduits coming from the reservoirs, stepwise gradients can be created and dispensed to the target areas. By associating a gradient pump (119) at the junction continuous and/or stepwise gradients can be formed.

Typically gradients are defined as a change in salt concentration, kind of salt, pH, composition of solvents and/or some other component/components that interferes/interfere with a biologically or chemical experiment which is carried out within a microsystem, preferably a microfluidic device.

Depending on the receiving structure (TA I) in the microfluidic disc and the kind of process that is to be carried out within the microsystem, for instance a microfluidic disc, the droplets should have a volume within the interval of $10^{-6}$–$10^0$ μl, for instance within $10^{-5}$–$10^{-1}$ μl. The frequency of droplets is typically such that a microchannel structure receives one droplet per revolution or every second or every third revolution or more rarely. A possible variant is to dispense several droplets per revolution in the same structure.

The optimal velocity of the droplet when leaving the dispenser orifice depends on many factors but should as rule of thumb be in the interval 0.5–25 m/sec, such as 1–10 m/sec.

The dispenser is mounted on a frame (not shown in FIGS. 1a and b) to keep it in a fixed angular position relative the trigger position (105). The dispenser may be movable inwards or outwards relative to the shaft (117) of the motor (115) (radial movement). A configuration allowing radial movement of the dispenser enables dispensation of droplets to target areas that are positioned at different radial distances from the center of the disc. By continuously moving the dispenser radially during spinning it is possible to dispense to target areas that are arranged in a spiral-like manner.

The arrangement may also have more than one dispenser. Several dispensers may be configured to an array for simultaneous dispensation to several target areas on a disc or other ways of coordinated dispensation. If two or more dispensers are present in the same arrangement the may act independently from each other.

c) Trigger Position

The trigger position (105) comprises a detector that is capable of detecting the trigger mark (104) on the disc (103) each time the mark passes the trigger position. Passage of the trigger mark may initiate a dispensing signal, typically via the controller. The system may provide for a predetermined delay between passage and actual dispensing ($T_{elec}$). This delay may be adjustable.

d) Controller

The controller (114) comprises, e.g. electronic and programmable control means with operator's interface and software, not further disclosed. The controller may be a separate physical part within the arrangement and/or may have parts that are physically associated with the units with which it communicates by sending and receiving signals. The controller (114) communicates with the spinner (113), the drop dispenser (110), and/or the detector in the trigger position (105), for instance.

The controller is capable of initiating the dispensing signal (106) after having received a triggering signal from the trigger position (105). The characteristics of the dispensing signal are defined by values programmed in step (ii) including values preset, for instance by the manufacturer, or, if needed, programmed during step (iii). The controller also controls when the dispensing signal (106) is sent to the dispenser, i.e. when the factual dispensation is taking place. A preferred way is to link the time at which the dispensing signal ejects a droplet to actually measuring that a target area is in a position permitting the droplet to hit the target area. If an encoder is linked to the spinning movement as discussed above, the encoder signal can be used to determine when an inlet port I (TA I) is in the correct position and also regulate so that the factual ejection of the droplet through the orifice takes place at the most appropriate time. If the encoder is high-resolving and used as suggested above, dispensation can take place with a high accuracy with respect to timing. An encoder also facilitates dispensation into target areas that are apart from each other by different angular distances.

Alternatively the time at which the dispensing signal is given is linked to the pre-programmed angular velocity of the disc, i.e. the angular velocity and the angular distances between the orifice and the trigger position and between the triggering mark and a target area, respectively, are used to calculate the time at which the dispensing signal shall actuate the dispenser. This way of controlling the dispensing has been found less accurate than the previous variant, for instance the encoder variant, because it will not account for variations that normally occur for preset spinning speeds. Steps (ii) and (iii).

For step (ii) the main dispensation parameters to be programmed are defined by the equations given above and/or depend on physico-chemical properties of the liquid as such. These parameters include:
(a) speed of rotation of the disc (angular velocity $\omega$),
(b) the revolutions under which dispensation is to take place and/or the frequency f of droplet dispensation to target area TA I,
(c) shape of the dispensing signal, for instance amplitude, and/or frequency f of dispensing pulses etc,
(d) delay $T_{elec}$ between the signal from the trigger position and the actual dispensing of a droplet,
(e) distance h between the dispenser orifice and the disc, and
(f) radial movement and/or radial position of the dispenser orifice.

The values of the parameters (a)–(f) are selected to give dispensation of the droplets to inlet port I (TA I).

The term "programmed" above includes that the user programs the controller and/or that the manufacturer has pre-programmed certain parameters.

Experiment 2 of the experimental part shows that a change in the physico-chemical characteristics of the liquid may influence the velocity with which a droplet leaves the dispenser orifice. Equation 2 illustrates that such a change can be compensated by altering one or more of the previously described variables (a), (c), (d) and (e). See for instance example 3 that illustrates that a change in the amplitude of the pulse/pulses of the dispensing signal can compensate a change in velocity.

Surface tension, density, viscosity, etc are physico-chemical characteristics that may change when the composition of a liquid is changed (gradient). Determination of the influence various parameters may have on droplet velocity can also be elucidated from separate experiments, for instance as illustrated in experiment 2 or from the pattern of where the droplets hit the disc surface during droplet dispensation, e.g. for a liquid containing a gradient. Appropriate changes in the shape of the dispensing pulses can be determined empirically as outlined in experiment 3 of the Experimental Part. Compensation functions or discrete values so found or compensation functions or values derived from equation 2 can then be programmed into the controller either in step (ii) or, if apprpriate during step (iii). Also manual adaptation of the velocity or trajectory path of the droplets during step (iii) can be carried out if the instrumentation is designed for this.

In the case the microfluidic disc comprises several inlet ports/target areas to which droplets are to be dispensed, the dispensing signal comprises several pulses at a frequency f, which is determined, as described in equation 4, by the angular distance (a) between the inlet ports/target areas and by the angular velocity ($\omega$) of the disc. The number of pulses is equal to the number of droplets to be formed for a dispensing signal and also equal to the number of inlet ports/target areas to which droplets shall be dispensed. Accordingly also in this case the controller is set to values for the parameters that will match each other so that the individual droplets ejected through the orifice by a dispensing signal will hit their intended inlet port, respectively. Typically the dispensing parameters are selected among (a)–(f) above.

Step (ii) also comprises programming characteristics of the microfluidic disc to be used. Such characteristics are number of inlet ports/target areas and their angular position and possibly also radial position if the dispenser is radially movable over a disc which is placed in the arrangement. The manufacturer preferably does the programming of disc specific characteristics so that the user only needs to program the kind of disc he intends to use.

Processes to be Performed within the Microsystems.

In each microchannel structure and/or target area, liquids are processed in order to carry out various miniaturised chemical and biological experiments, i.e. assay protocol, synthesis protocol, cell culturing protocols etc within the chemical and biological field including biochemistry, chemistry, biophysics, microbiology, medicine, zoology, molecular biology etc. Processing includes that various chemical reactions and/or biochemical reactions and/or biological reactions etc are taking place. Typical protocols utilise specific reactions between reactants having mutual affinity to each other leading to
(a) formation of an affinity complex that is immobilized to a solid phase in a detection and/or reaction microcavity or
(b) one or more other reaction products that may be soluble or insoluble in the detection microcavity.

Typical detection principles are based on radioactivity, fluorescence, chemiluminescence, bioluminescence, enzymatic activity, chromogens, light scattering (turbidometry) etc, for instance by utilizing reactants that exhibits groups providing the corresponding properties or groups that can be transformed to one of these groups.

Typical reactants in this context are individual members of affinity pairs such as (a) antigen/hapten and the corresponding antibody including its antibody active fragments, (b) lectin and the corresponding carbohydrate structure, (c) native ligands and the corresponding native receptors, (d) complementary nucleic acids including synthetic variants such as synthetic oligonucleotides and variants that are capable of mimicking hybridisation (e.g. PNAs), (e) Ig(Fc)-binding proteins and Protein A, Protein G and other Ig(Fc)-receptors, (f) ion pairs of opposite charges, enzyme and the corresponding substrate, inhibitor, cofactor, coenzyme etc that can bind to the enzyme, (g) ligand and receptors that are involved in cell surface interactions etc Synthetic variants that more or less mimic a member of a native affinity pair are also included.

The reaction microcavity may contain a separation medium in the form of a porous bed through which a sample liquid containing at least a substance that is capable of binding to the bed under the conditions applied is passing. During the passage, the substance(s) becomes (become) bound and non-binding substances pass through. Subsequently an eluent may be applied through the bed so that one or more of said at least one substance are released from the bed. Further processing may take place on one or more of the non-binding substances after their passage through the bed, and/or on one or more of said at least one substance while being bound to or subsequent to their release from the bed. Possibly one or more washing liquids may be passed through the bed after the sample liquid but before the eluent. The various liquids used in this kind of protocol may be applied through the same inlet port/target area or through different inlet ports/target areas At least one of the liquids is dispensed to an inlet port in accordance with the invention. The eluent can be in the form of a continuous or a stepwise gradient of the kind discussed elsewhere in this text.

Further processing may be detection of a substance bound to the bed or of a non-binding substance passing through the bed.

The porous bed discussed above may be a porous monolith or a packed bed of porous or non-porous particles. The population of particles defining the bed may be in bead form and/or be monosized (monodispersed) or polysized (polydispersed). By the term monosized is meant that 95% of the particles are within the interval of the mean particle size±5%. Populations having other particle distributions are polysized.

The reaction microcavities may also be used as "fermentors" for the growing of cells, in cell based assays, in the synthesis of organic and inorganic compounds etc. Growing of cells includes cell culturing of anchorage or non-anchorage dependent cells and tissue culturing. The innovative method of dispensing may be used for adding cells, reagents and the like to the reaction microcavity. It may also be used for gradually replacing a liquid already present in the reaction microcavity.

What has been said above for reaction microcavities in microfluidic discs may also apply to target areas of non-fluidic microsystems.

The invention is further defined in the patent claims that are part of the description. The invention will now be illustrated in the Experimental Part.

Experimental Part

The microfluidic disc used had been manufactured in transparent plastic material by injection moulding and covered by a lid as outlined under the heading "Microfluidic Disc and Processes to be Performed".

Experiment 1. Investigation of the Flow Profile Deformation Occurring Between the Pump and the Dispenser.

Experimental: The experimental set up was as in FIG. 1 except that the droplets were not collected in the microfluidic device. Colorimetry, with Cibacron dye (Brillant Red 4B-E, Ciba) in water was used to investigate gradients (from water up to 70% of the Cibacron solution applied over 1, 2 or 3 minutes) with different flow rates (0.1 and 0.5 ml/min). The process was monitored by collecting 500 droplets at predetermined intervals and measuring the colour intensity of the collected samples.

Results: FIG. 3 shows four gradients obtained from the dispenser. The result shown demonstrates the reproducibility of a 1 minute gradient at a flow rate of 0.3 ml/min. This graph shows that the gradient is obtained after 90 seconds indicating a lag time of 30 s with in the current configuration.

Experiment 2. Velocity of the Droplet as a Function of the Gradient with a Constant Pulse.

Experimental: The experimental set up was as in FIG. 1 except that the droplets were not collected in the microfluidic device. The variation in drop velocity v (m/s) with an acetonitrile gradient (0–80%) or a salt gradient 250 mM Tris-HCl pH 8 (0–1.5 M NaCl) was studied. The velocity was measured using a computer IR-camera system (Sydat Automation, Sweden) developed for evaluation of ink-jet print heads.

Results: Se FIG. 4. The physical properties of the dispensed liquid vary with the gradient profile and clearly affect the velocity of the droplets, leading to misalignment. However, this misalignment can be compensated for by adjusting various parameters, for example the trigger delay or the disc angular velocity (see equations 2 & 3) can be modified, although adjusting the angular velocity may affect flow control (see also FIG. 5).

For comparison when the disc is spun at 1500 rpm, the velocity of a point over the disc at a distance of 30 mm from the centre is 4.7 m/s.

Experiment 3. Velocity of the Droplet as a Function of the Pulse Amplitude.

Experimental: The experimental set up was as in FIG. 1 except that the droplets were not collected in the microfluidic device. The drop velocity v (m/s) was studied as a function of the pulse amplitude for normal and high salt buffer solutions.

Results: By adjusting the pulse amplitude it is possible to adjust the drop velocity and thus to solve the misalignment problem.

Experiment 4. Stepwise Elution of Cy5 Labelled Angiotensin I from Nanoliter Columns on a Disc.

Experimental: Columns (30 and 35 nanoliters in volume) were packed with SOURCE® 15RPC (Amersham Pharmacia Biotech, Sweden) by centrifugation into disc microstructures. The microchannel structures used are given in FIG. 2. Packing was accomplished by filling a suspension of the bead material into inlet ports (210). Upon centrifugation, the beads collect in the deeper part of the lower shank (214) of the Y-shaped structure. Peptides (angiotensin I and II) were labelled using a Cy3 or Cy5 labelling kit (Amersham Pharmacia Biotech, Sweden). The columns were conditioned by applying 2×500 nl 50% acetonitrile, 0.1% TFA and washed twice with 500 nl of 0.1% TFA under controlled spinning (1500 rpm) by filling the common distribution channel (202) via inlet port (203) and spinning for each solution. A 500 nl mix of Cy5-labelled angiotensin I (110 nM—Sigma) and Cy3-labeled angiotensin II (880 nM—Sigma) was loaded via inlet port (203) to the common distribution channel (202) and a stepwise increase in spin speed. Bound components were eluted with a step gradient between 12.5–37.5% acetonitrile. Portions corresponding to increasing concentrations of acetonitrile were filled into the common distribution (202) by pipetting and passed through the columns by spinning the disc. The acetonitrile concentration was increased by 2.5% in each 200 nl step and applied with a controlled spin flow (1500 rpm). The separation in the columns was monitored using a fluorescence microscope.

Results: The separation of labelled peptides and free dyes has been reproduced successfully on 16 columns processed simultaneously on a disc (results not shown). This result is not linked to the dispensation of the solutions by pipetting. One can envisage that dispensation can also take place according to the invention by droplet dispensation to inlet ports (210).

Experiment 5. Gradient Elution on a Nanoliter Column in a Disc.

Experimental: The experimental set up was according to FIG. 1. Columns (34 and 38 nanoliters in volume) were packed and conditioned as described in example 4. A ix of Cy3 (700 nM)/Cy5 (300 nM) dye (500 nl) was loaded by a stepwise increase in pin speed. The continuous gradient elution was made using a dispenser with a nozzle 60 μm in diameter and a flow-through channel 1 mm wide and 50 μm in depth. Dispensation of the gradient was according to the invention through inlet port (210). Various elution profiles were tested using a dispenser frequency of 1 kHz and spinning between 2500 and 1800 rpm. The separation was monitored in the columns by a fluorescence microscope.

Results: The results indicated the beginning of a separation of Cy3 and Cy5 dyes using a gradient 0–40% acetonitrile, 0.1% TFA over 1 minute. Other experiments have shown the possibility to dispense a gradient while spinning into 14 microstructures using various liquids such as water, acetonitrile mixes and Tris buffer (1 kHz pulse and 1500 rpm).

This example illustrates that a detector that is capable of detecting the reaction in a reaction and/or detection microcavity can be linked to the arrangement and used to monitor the proceedings of the reaction. In this case reaction is adsorption/desorption to the separation media. The detectors used may be of the same kind as outlined in our copending patent application SE 0103118-6, which corresponds to U.S. provisional application No. 60/322,622, both filed Sep. 17, 2001 (Gyros AB, Magnus Ljungström et el) that hereby is incorporated by reference.

What is claimed is:

1. A method for dispensing droplets of a liquid to a microsystem in the form of a disc having a target area (TA$^O$I) in its surface which comprises the steps of:
   i) providing (1) said disc which has a triggering mark, and
   (2) a dispenser arrangement comprising:
      a) a spinner for rotating the disc around its axis,
      b) a drop dispenser permitting dispensation of droplets from a dispenser orifice of said drop dispenser to the target area TA$^O$I,
      c) a fixed trigger position outside the disc, and
      d) a controller which is capable of triggering a dispensing signal, which causes dispensation of one or more droplets from said dispenser orifice into the target area (TA$^O$I) as a function of the triggering mark passing the trigger position,
   ii) placing the disc in the spinner and programming the controller with values for one or more dispensing parameters that will give dispensation of the droplets to the target area TA$^O$I, and
   iii) dispensing the droplets while spinning the disc.

2. The method of claim 1, wherein said parameters are selected from the group consisting of
   (a) speed of rotation of the disc (angular velocity $\bar{\omega}$),
   (b) the revolutions under which dispensation is to take place and/or the frequency f of droplet dispensation to the target area TA$^O$I,
   (c) shape of the dispensing signal,
   (d) delay $T_{elec}$ between the signal from the trigger position and the actual dispensing of a droplet,
   (e) distance h between the dispenser orifice and the disc, and
   (f) radial movement and/or radial position of the dispenser orifice.

3. The method of claim 2, wherein
   i) the liquid comprises a gradient with respect to at least one of its constituents; and
      ii) that the value for at least one of the parameters (a), (c), (d), and (e) is adjusted during the dispensation to compensate for the change in velocity of the droplets which possibly is caused by the gradient.

4. The method of claim 3, wherein said adjustment is handled by the controller.

5. The method of claim 2, wherein the shape of the dispensing signal is programmed to comprise a number of pulses such that each droplet formed will correspond to a pulse and that the programmed values for the remaining parameters (a)–(f) will be such that for each dispensing signal at most one droplet per revolution will be dispensed into each of said one or more target areas.

6. The method of claim 2, wherein said shape is amplitude, and/or frequency f of dispensing pulses.

7. The method of claim 1, wherein the disc is a microfluidic disc having a microchannel structure I comprising
   a) an inlet port that is equal to the target area TA$^O$I, and
   b) a microcavity positioned downstream to the target area TA$^O$I and used for carrying out a chemical or biological experiment.

8. The method of claim 7, wherein said liquid comprises a gradient which is defined as a change in salt concentration, kind of salt, pH, composition of solvents and/or some other component/components that interferes/interfere with an experiment which is carried out in the microcavity.

9. The method of claim 7, wherein the microcavity contains a separation media in the form of a porous bed.

10. The method of claim 9, wherein the method comprises
    a) dispensing a liquid sample (liquid 1) to a sample inlet port of said microchannel structure I, which sample contains at least one substance that is capable of binding to the bed when passing through it, and
    b) subsequently dispensing an eluent (liquid 2) to an inlet port of said microchannel structure I for releasing at least a portion of said at least one substance from the separation medium,
    wherein at least one of said inlet ports being is the target area TA$^O$I, and at least one of liquid 1 and liquid 2 is dispensed to said target area TA$^O$I as droplets through said drop dispenser by using said programmed values for the dispensing parameters, and wherein liquid 1 is before liquid 2 through said microcacvity.

11. The method of claim 10, wherein in that the eluent comprises a gradient with respect to one of its constituents.

12. The method of claim 9, wherein the porous bed is a porous monolith or a packed bed of porous or non-porous particles.

13. The method of claim 12, wherein the particles are in beaded form and/or are monosized (monodispersed) or polysized (polydispersed).

14. The method of claim 1, wherein
a) the spinner is linked to an encoder which gives at least 10,000 grades per revolution, and
b) the time at which the dispensing signal is given is determined by the number of encoder grades between the triggering mark and the triggering position.

15. The method of claim 1, wherein the time at which the dispensing signal is given is calculated from the speed of rotation (angular velocity) and the time at which the triggering mark passes the trigger position.

16. The method of claim 1, wherein a piezo-driven actuator drives the dispenser which is actuated according to the dispensing signal.

17. The method of claim 1, wherein the dispenser is a flow-through dispenser.

18. The method of claim 1, wherein the disc comprises one, two or more additional target areas ($TA^1I$, $TA^2I$, $TA^3I$ etc) which are at the same radial distance from the disc centre as target area $TA^0I$.

19. The method of claim 18, wherein the disc is a microfluid disc comprising two or more microchannel structures which each comprises an inlet port which is a target area selected among the target areas.

20. The method of claim 18, wherein the angular distances between the target areas that are located next to each other are the same or different.

21. The method of claim 1, wherein
a) the dispenser arrangement comprises an array of dispensers that are under control of the controller; and
b) said drop dispenser is one of said dispensers.

22. The method of claim 1, wherein said disc is a microfluidic disc comprising a microchannel structure I with an inlet port that is equal to said target are.

23. The method of claim 1, wherein said triggering mark is placed in the circumference of the disc.

24. An arrangement enabling dispensation of droplets of a liquid to a microsystem in the form of a spinning disc comprising a target area ($TA^0I$) in its surface for the droplets, wherein the arrangement comprises:

a) a spinner for rotating the disc around its axis, b) a drop dispenser permitting dispensation of droplets to target area $TA^0I$ from a dispenser orifice of said drop dispenser to target area $TA^0I$, c) a fixed trigger position positioned outside the disc and comprising a detector which is capable of detecting a triggering mark passing the trigger position when the disc is placed in the spinner and rotated, and d) a controller which is capable of triggering a dispensing signal for the dispensation of a droplet into target area $TA^0I$ as a function of the triggering mark passing the trigger position.

25. The arrangement of claim 24, wherein said disc is a microfluidic disc comprising a microchannel structure I with an inlet port that corresponds to target area $TA^0I$.

* * * * *